US005529075A

United States Patent [19]
Clark

[11] Patent Number: 5,529,075
[45] Date of Patent: Jun. 25, 1996

[54] FIXATION DEVICE AND METHOD FOR REPAIR OF PRONOUNCED HALLUX VALGUS

[76] Inventor: David Clark, 106 Le Grande, Aurora, Ill. 60506

[21] Appl. No.: 304,167

[22] Filed: Sep. 12, 1994

[51] Int. Cl.[6] .................................................. A61B 19/00
[52] U.S. Cl. ............................................ 128/898; 606/72
[58] Field of Search ................................ 606/60, 72, 73, 606/80, 86, 96, 105; 623/21; 128/898; 411/433, 324, 280

[56] References Cited

U.S. PATENT DOCUMENTS

| | | | |
|---|---|---|---|
| 3,199,564 | 8/1965 | Waelz | 411/280 |
| 3,809,075 | 5/1974 | Matles . | |
| 4,033,394 | 7/1977 | Capuano | 411/433 |
| 4,156,296 | 5/1979 | Johnson et al . | |
| 4,159,716 | 7/1979 | Borchers . | |
| 4,642,122 | 2/1987 | Steffee . | |
| 4,731,087 | 3/1988 | Sculco et al. . | |
| 4,787,908 | 11/1988 | Wyss et al. . | |
| 4,908,031 | 3/1990 | Frisch . | |
| 4,969,909 | 11/1990 | Barouk . | |
| 5,207,712 | 5/1993 | Cohen . | |
| 5,250,049 | 10/1993 | Michael | 606/72 |

OTHER PUBLICATIONS

Mann (Ed.), Surgery of the Foot, 65 (5th ed. 1986).
Bonney and McNab, "Hallux Valgus and Hallux Rigidus," vol. 34–B, No. 3, Aug. 1952, pp. 366–385.
Jahss et al., 1985, "Roentgenographic and Mathematical Analysis of First Metatarsal Osteotomies for Metatarsus Primus Varus: A Comparative Study," Foot & Ankle, vol. 5, No. 6, pp. 280–321.
Sammarco et al., 1993, "Bunion Correction Using Proximal Chevron Osteotomy," Foot & Ankle, vol. 14, No. 1/Jan. 1993, pp. 8–14.
Kummer, 1989, "Mathematical Analysis of First Metatarsal Osteotomies," Foot & Ankle, vol. 9, No. 6/Jun. 1989, pp. 281–289.
Resch et al., "Proximal Closing Wedge Osteotomy and Adductor Tenotomy for Treatment of Hallux Valgus," Foot & Ankle, vol. 9, No. 6/Jun. 1989, pp. 272–280.

*Primary Examiner*—Stephen C. Pellegrino
*Assistant Examiner*—Scott B. Markow
*Attorney, Agent, or Firm*—Banner & Allegretti, Ltd.

[57] ABSTRACT

A method is described to repair hallux valgus which involves a medial incision as the primary incision, mechanical stabilization of the first and second metatarsals during and after a proximal chevron osteotomy of the first metatarsal shaft, reorientation of the metatarsal segments to compensate for hallux valgus, and stabilization of the reoriented metatarsal during healing by insertion of a fixation device which may be removed later with little trauma to surrounding tissues. The fixation device comprises an elongated, relatively rigid stabilizing member of biocompatible material sized to pass from the medial side of the first metatarsal through the first and second metatarsals and out the lateral side of the second metatarsal, and two retainer members cooperating with the segments of the stabilizing member, medial to the first metatarsal and lateral to the second, adapted to prevent migration of the stabilizing member as the wound is healing.

10 Claims, 3 Drawing Sheets

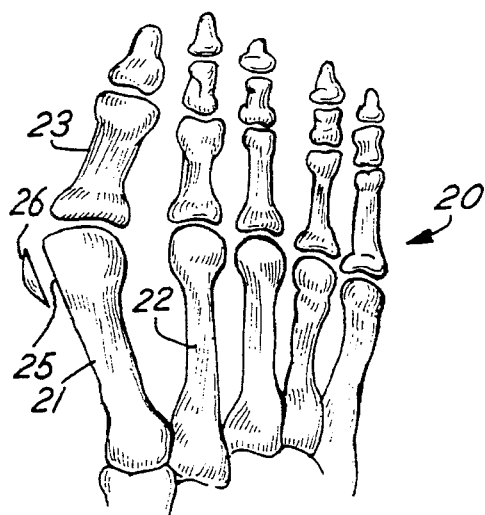
FIG.3
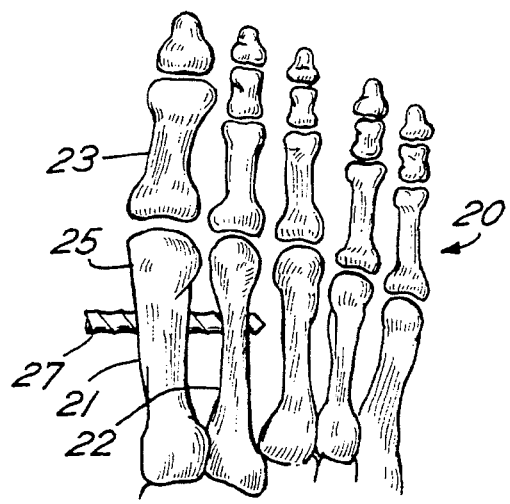
FIG.4
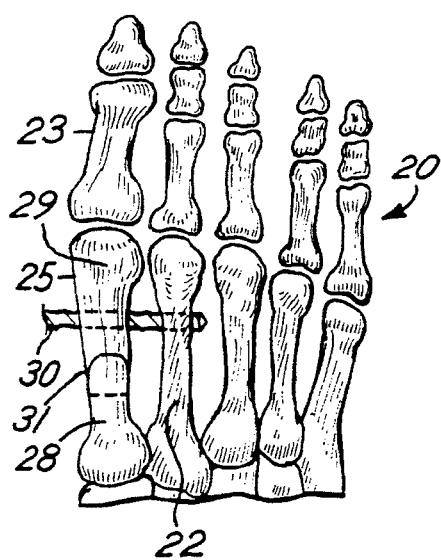
FIG.5
FIG.6
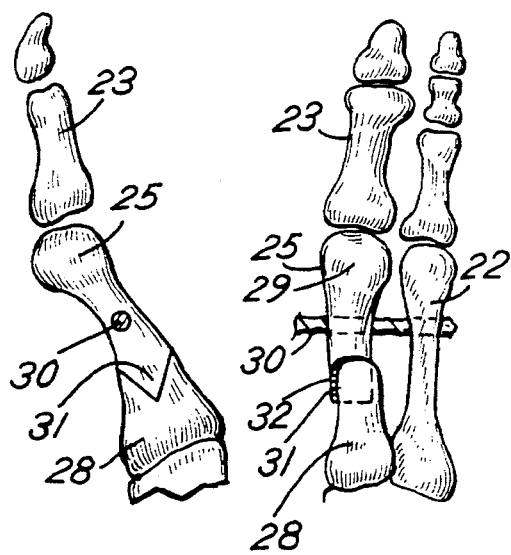
FIG.7
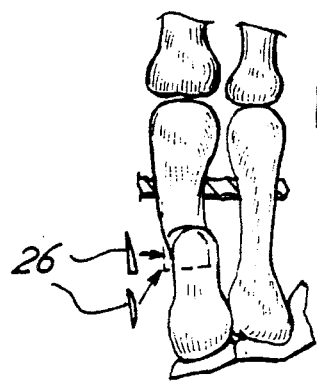
FIG.8

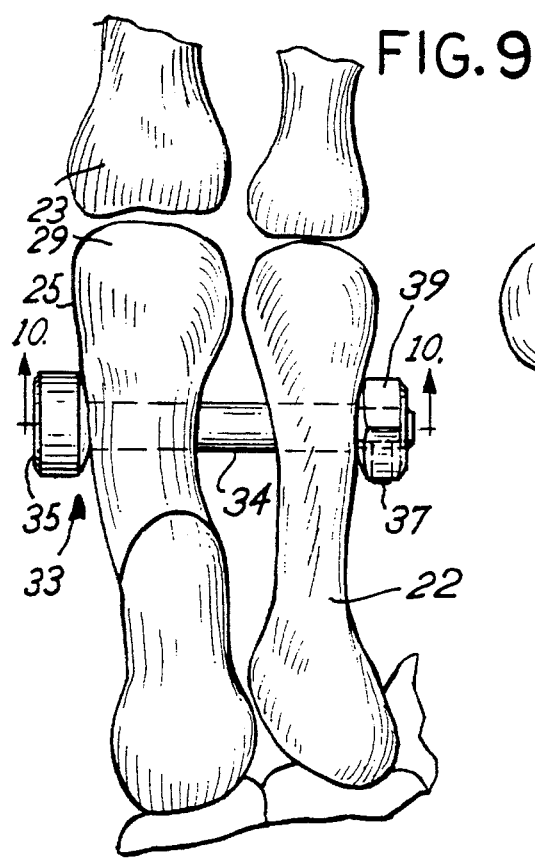
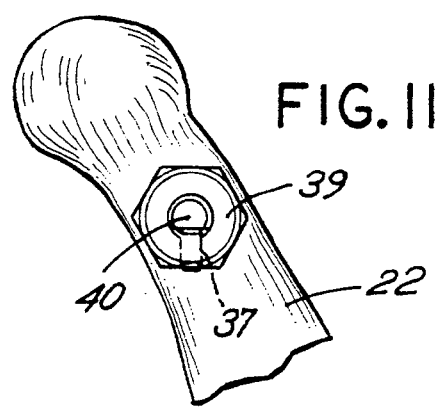
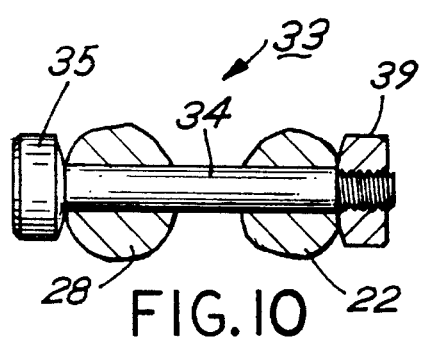
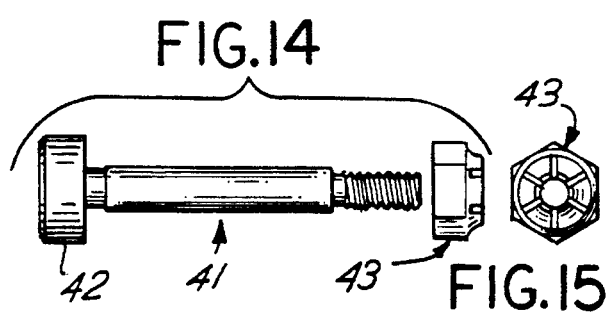
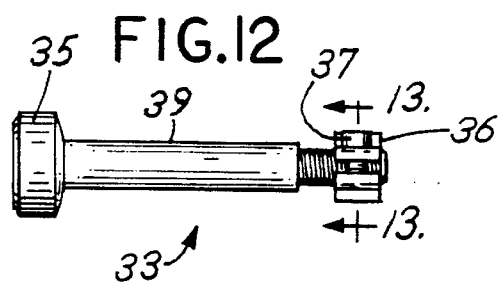
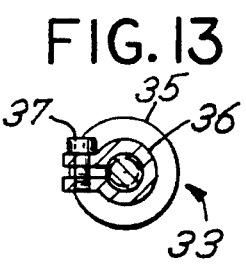

FIXATION DEVICE AND METHOD FOR REPAIR OF PRONOUNCED HALLUX VALGUS

BACKGROUND OF THE INVENTION

1. Field of the Invention

This invention relates to a specific subset of the field of orthopedic surgery, namely, to devices and methods for the repair of pronounced bunion deformities, scientifically known as hallux valgus.

Hallux valgus is a deformity of the forefoot involving multiple components. It has been described as "static subluxation of the first metatarsophalangeal joint with lateral deviation of the great toe and medial deviation of the first metatarsal. It is occasionally accompanied by rotation or pronation of the great toe in severe cases." See Mann (Ed.), Surgery of the Foot 65 (5th ed. 1986).

One of the common causes of hallux valgus is prolonged deformation of the foot inside so-called high fashion shoes commonly worn by women. In such shoes, the great toe sits in an abnormal orientation for a long period of time, which eventually stretches out the joint capsule, in turn promoting migration of the muscles into an abnormal position. Thus, women have bunions many times more commonly than men do. Other factors which predispose patients to hallux valgus are rounded unstable metatarsophalangeal joint surfaces and oblique joint surfaces at the proximal first metatarsal joint.

In the production of hallux valgus deformity, a point is reached in which the muscles migrate laterally outside the joint line. Once this stage has been reached, the deformity is self-feeding and becomes inevitably worse.

The severity of hallux valgus deformities has traditionally been quantified in a variety of ways based on measurements from x-ray pictures. The first of the two most common measurement or quantification techniques for hallux valgus is the so-called IM or intermetatarsal angle between the line of the first and second metatarsal shafts. This angle is normally about six degrees; the upper limit of normal is about nine degrees. The second measurement is the hallux valgus angle, which is the angle between the first metatarsal shaft and the proximal phalanx. This would normally be about nine or ten degrees maximum. A measurement of 12 degrees would be almost uniformly regarded as abnormal. A typical hallux valgus patient might have an IM angle of 15 degrees and a hallux valgus ("HV") of 35 degrees.

2. Description of the Prior Art

Historically, many different procedures have been proposed to correct hallux valgus deformities. One such technique is the simple exostectomy, which is merely an excision of the prominent medial eminence of the first metatarsal head. This technique has limited usefulness. Kotzenberg in Germany, roughly a hundred years ago, described a side (medial) entry and proximal V-cut or chevron osteotomy repair of hallux valgus. In the early part of the 20th century, an operation was reported in which the exostosis of the medial eminence bone was used as a bone graft with a proximal opening wedge osteotomy. McNabb and Bonney at the National Orthopedic Hospital in London described a procedure in the 1940's including an opening wedge proximal osteotomy and graft with cross-metatarsal screw fixation.

Today, there are two groups of operations which are commonly done to correct hallux valgus and associated deformities. Review of the literature and surgical experience indicate that a five-degree correction of the intermetatarsal angle and a maximum of ten-degree correction of the hallux valgus is reproducibly possible with distal osteotomy procedures of which the commonly used ones have been the Mitchell and more recently the distal chevron osteotomy.

The second currently common operation for correction is the Roger Mann proximal osteotomy of the metatarsal shaft. The Mann technique is used for somewhat more severe bunionectomies and involves a soft tissue release distally in which the intermetatarsal ligament, the adductor hallucis and the capsule of the metatarsal phalangeal joint on its fibular side are cut. Then the osteotomy is done proximally permitting correction to be obtained. The two segments of the displaced first metatarsal shaft are fixed to each other with a pin inserted at an oblique angle. Presently, Mann employs a simple orthopedic threaded screw between the segments of the first metatarsal shaft, instead of the pin. The Mann osteotomy necessitates a certain incidence of nerve injury; at least 10 percent numb toes typically result.

The choice of repair from among the prior art procedures is to some degree guided by the IM and HV angles preoperatively. However, the surgical techniques described above are of questionable suitability for repairs of the more severe cases as the corrections are borderline in such instances. For example, given a preoperative IM angle of 15 and an HV angle of 30, a distal procedure is barely going to correct that down into the normal range. Likewise, in the more severe cases, the Mann distal soft tissue procedure with proximal osteotomy does not always produce a satisfactory correction of the deformity. Malunion and non-union have also been recorded for both types of repairs.

Turning to the patent literature, U.S. Pat. No. 4,159,716 to Borchers describes a clamp apparatus and method for compressing and realigning bone structures to correct splay foot. U.S. Pat. No. 3,809,075 to Matles teaches wire or pin bone splints having at least one unitary hinged retainer of soft bendable material with wings adapted to detachably secure the member to a selected location on the wire or pin. U.S. Pat. No. 4,969,909 to Barouk describes a bent ended pin for longitudinal insertion into the medullary canals of a digit with a cup shaped adaptation at the articulation position between two bones. Toe prostheses useful at the metatarsal/phalangeal joint are fairly widely described in the patent literature, but offer little guidance in the, repair of hallux valgus. See U.S. Pat. Nos. 4,908,031 to Fisch; 4,787,908 to Wyss; 4,731,087 to Sculco et al.; 4,642,122 to Steffee; and 4,156,296 to Johnson et al.

SUMMARY OF THE INVENTION

Thus, there is a need for a technique and associated devices for repair of hallux valgus which can successfully correct the more severe cases.

It is an advantage of the present invention that it provides a stronger repair for hallux valgus, particularly during the immediate post-operative healing stage.

It is a further advantage of the instant invention that it addresses and helps to mediate the hallux valgus associated deformity of rotation of the metatarsal head.

It is an additional advantage of the invention that the primary incision is through the medial aspect of the foot, rather than the dorsal aspect, thus avoiding much of the risk to vascular and nervous tissue.

It is a further advantage and object of the present invention that it contemplates use of a fixation device during healing which does not loosen significantly or work its way out of position when the patient walks or engages in other movement.

The invention includes an operative procedure or method for repair of hallux valgus. Preferably, the invention comprises performing a soft tissue release through a small incision on the dorsum of the affected foot. Most preferably, a skin incision is made on the dorsum of the foot allowing exposure of the first intermetatarsal structures and the neck of the second metatarsal.

The distal soft tissue procedure then preferably involves release of the adductor halluces and the flexor halluces brevis as they are elevated from the lateral sesamoid and released from their attachment to the fibular side of the first proximal phalanx. This is followed by a capsulotomy of the fibular side of the metatarsophalangeal joint and exposure of the fibular side of the first metatarsal neck and the tibial and fibular sides of the second metatarsal neck.

The inventive surgical procedure comprises as a primary incision a medial incision at the first metatarsal. This medial incision preferably begins halfway between the metatarsophalangeal joint and the interphalangeal joint on the medial aspect of the foot and extends proximally to the first cuneiform halfway between the dorsal and lateral surfaces. The medial eminence of the first metatarsal head is then deeply exposed and excised. The foot is manipulated to correct the pronation deformity of the first metatarsal and maintain the proper plantar displacement of the first metatarsal head.

The first and second metatarsals are mechanically linked or splinted together, preferably by transverse pinning at the necks, to maintain the proper orientation of the first metatarsal during the remainder of the surgery. A proximal chevron osteotomy is performed on the first metatarsal shaft dividing it into two metatarsal segments. The metatarsal segments are then reoriented relative to each other to compensate for the metatarsus primus varus, thereby creating a medial dislocation gap at the terminus of the reoriented osteotomy surfaces. At least a portion of the excised medial eminence is grafted into this medial dislocation gap, with fixation of the proximal chevron osteotomy, if needed. The reoriented first metatarsal is then stabilized for healing by insertion of a fixation device which splints the first metatarsal to the second metatarsal and which is removable after healing, with limited trauma to surrounding tissue. Following a healing period, the fixation device is preferably removed.

Thus, the invention also contemplates a fixation device for use in the surgical correction of hallux valgus comprising an elongated relatively rigid stabilizing member sized to pass transversely from the medial side of the first metatarsal through the first and second metatarsals and out the lateral side of the second metatarsal in order to link the surgically repaired first metatarsal to the second and splint the former. The fixation device further comprises two retainer members which cooperate with the segments of the stabilizing member which are medial to the first metatarsal and lateral to the second metatarsal in such a way as to prevent migration of the stabilizing member out of the bone. The stabilizing and retaining members are configured such that the entire fixation device is surgically removable with two or fewer incisions, engendering the minimum amount of trauma to surrounding tissues. Most preferably, the fixation device is a bolt with medial head and lateral removable or releasable locking means.

BRIEF DESCRIPTION OF THE DRAWINGS

FIG. 3 illustrates the excision of the medial eminence of the first metatarsal head of a foot afflicted with hallux valgus.

FIG. 4 is a dorsal view of a drill bit transversely piercing the first and second metatarsals as part of the inventive repair for hallux valgus.

FIG. 5 illustrates the proximal chevron osteotomy cut in the first metatarsal and the concomitant splinting of the first metatarsal to the second metatarsal.

FIG. 6 is a medial view of FIG. 5.

FIG. 7 illustrates the process of corrective manipulation and displacement at the osteotomy of the first metatarsal segments while the first and second metatarsals are splinted together.

FIG. 8 depicts the insertion of the bone graft in the medial gap at the osteotomy site.

FIG. 9 shows the fixation device inserted for healing splinting the first metatarsal to the second metatarsal.

FIG. 10 is a sectional view along the lines 10—10 of FIG. 9.

FIG. 11 is a lateral end view of a portion of FIG. 9 showing the side of the second metatarsal with the second retainer member illustrated.

FIG. 12 shows an alternative fixation device with a preferred second retainer member.

FIG. 13 is a lateral end view of a portion of FIG. 12 showing the second retainer member.

FIG. 14 depicts another alternative fixation device with a highly preferred second retainer member.

FIG. 15 shows a lateral end view of a portion of FIG. 14 illustrating the second retainer member.

DESCRIPTION OF THE PREFERRED EMBODIMENTS

Figure 1:
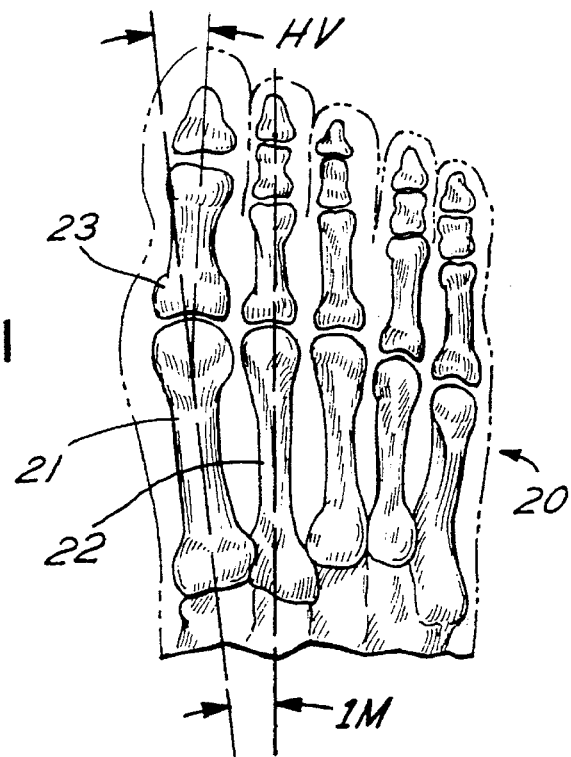
FIG. 1 is a dorsal view of the bones of a normal right forefoot with the intermetatarsal and hallux valgus angles indicated.

Within the scope of the invention as summarized above, a number of variations are possible in the inventive procedure for repair of hallux valgus. Good surgical techniques and practices should be employed throughout the procedure. As will be understood by one of ordinary skill in the art, a choice of anesthetic techniques may be used prior to and during the surgery to alleviate the patient's discomfort. As will also be understood by one of ordinary skill in orthopedic surgery, proper sterile techniques should be observed in prepping the patient, performing the surgery and closing afterwards. Appropriate surgical/orthopedic instrumentation should be available and sterilized before surgery commences, including drills, saws, retractors, needles and suture materials.

The actual inventive surgical procedure for repair of hallux valgus preferably commences with a soft tissue release through a small dorsal incision. More preferably, the distal soft tissue procedure involves release of the adductor hallucis and the flexor hallucis brevis as they are elevated from the lateral sesamoid and released from their attachment to the fibular side of the first proximal phalanx. This is followed by a capsulotomy of the fibular side of the metatarsophalangeal joint and exposure of the fibular side of the first metatarsal neck and the tibial and fibular sides of the second metatarsal neck.

A primary incision is then made medially at the first metatarsal. The dorsum of the foot is rich in blood vessels and nerve tissue, and the medial incision has the advantage that it avoids much of the risk to vascular and nervous tissue which is associated with prior art dorsal entries.

In accordance with the invention the medial eminence of the first metatarsal head is then exposed and excised. Preferably at this point, the foot is manipulated to reorient the first metatarsal into the desired corrected position. The reorientation position will be dependent to some extent on the anatomy of the patient and the severity of the hallux valgus deformity.

Thereafter, it is desirable to splint the first metatarsal to the second to maintain the former in proper position and orientation during the remainder of the surgery. This is accomplished, preferably, by drilling a hole from the medial side of the first metatarsal transversely through the bone approximately on the diameter of the cross section and out the lateral side, and similarly from the medial to the lateral side of the second metatarsal and out the lateral side. The hole should be relatively small in diameter compared with the diametral sizes of the bones so as to minimize the injury to the bony tissue, and the holes through the two metatarsals should be aligned with each other when the first metatarsal is reoriented to its desired corrected position. Preferably, the holes are drilled distally in the metatarsals.

The reorientation of the first metatarsal is stabilized for the remainder of the procedure by the insertion of a stabilization device, usually a metallic, composite or ceramic pin, which splints the first metatarsal to the second metatarsal. Alternatively, the drill bit itself may act as the intraoperative splint, or the fixation device to be used during the healing phase following surgery may be inserted at this point to act as the intraoperative stabilizing means. In other words, the invention preferably contemplates intermetatarsal pinning at a distal location for the duration of the surgery. The "pin" acts as a rail along which the corrective translation of the bunionectomy may be performed.

A proximal chevron osteotomy is performed on the first metatarsal shaft (forming two metatarsal segments). The metatarsal segments are then reoriented relative to each other to compensate for the hallux valgus. In other words, the first metatarsal while fixed in the derotated position, is slid over at the osteotomy to provide the desired correction. As will be understood by one of skill in the art, this procedure creates a dislocation gap at the medial terminus of the reoriented osteotomy. At least a portion of the medial eminence of the first metatarsal is grafted into the medial gap created by the osteotomy/reorientation and the osteotomy cum graft is retained in position by pin or screw fixation if necessary.

The reorientation of the first metatarsal is stabilized for healing by insertion, preferably through the previously drilled distal diametral holes piercing the first and second metatarsals, of a fixation device which mechanically links or splints the first metatarsal to the second metatarsal. This fixation device should be removable after healing with limited trauma to surrounding tissue. The fixation device must be sterile, and biocompatible for at least the duration of the healing period. It should be relatively rigid and of a strong enough material to withstand the forces which will be imparted to it when the patient walks and otherwise engages in normal movement during the healing phase. The portion of the fixation device which passes through the metatarsal bones should be relatively narrow in diameter as compared with the diameters of the first and second metatarsals, and the fixation device and should be sized so as to span the distance from the medial side of the first metatarsal and out the lateral side of the second metatarsal when the bones have been reoriented in the corrected fashion. Materials which may be employed for the fixation device include stainless steel (surgical grade), titanium alloys, cobalt/chromium/molybdenum alloys and other orthopedic materials which will be apparent to one of ordinary skill in the art. The chosen material should not rust or create an electrolytic cell, and is preferably non-magnetic.

Preferably, a K wire is employed to act as the stabilization device and between the metatarsals during the surgery. In the preferred embodiment, before closing, the K wire is replaced with a fixation device such as a bolt having a head located medially to the first metatarsal to retain its position. The bolt projects laterally beyond the second metatarsal neck and is fixed there with a locking means. Preferably, the bolt is threaded at its lateral end, and the locking means is a C-clamp with tightening screw which grips the lateral end of the bolt. Alternatively, the bolt may have a flattened longitudinal segment at its lateral end, and may be fitted when in position with a nut having a locking screw therethrough to lock the nut in position on a flat surface of the bolt. Most preferably, the bolt is an appropriately dimensioned shoulder bolt, threaded at its lateral end, and the locking means is a self-locking castle nut sized to cooperate with the threading on the bolt. Optionally, the bolt may be cannulated so that it can be slipped over the K wire or other stabilization device and slid easily along the wire so as to be positioned for fixation of the first and second metatarsals. Other alternatives will be apparent from the instant specification.

The capsule repair is completed, the incision closed, and the foot casted if necessary. After a healing period, the patient may return for removal of the fixation device. The bolt with C-clamp or locking nut or other retainer member is removed surgically and requires at most two incisions to accomplish the removal. Typically, the surgeon would make a small lateral incision to remove the locking nut and a small medial incision to extract the bolt.

The most preferred embodiment of the inventive surgical procedure for repair of hallux valgus is as follows:

Skin Incision One

An incision is made on the dorsum of the foot, beginning at the proximal end of the first web space, extending proximally in the midline between the first and second metatarsal heads, and then heading 45 degrees laterally and proximally beyond the extensor digitorum tendon of the second toe.

Distal Soft Tissue Procedure

In the incision between the first and second metatarsal necks, the adductor hallucis and the flexor hallucis brevis are elevated from the lateral sesamoid, then released from the fibular side of the first proximal phalanx. Capsulotomy of the fibular side of the first metatarsophalangeal joint and manipulation into slight varus are then accomplished. Exposure of the fibular side of the first metatarsal neck and of the tibial and fibular sides of the second metatarsal neck is performed through the more proximal part of the incision.

Skin Incision Two

A medial incision is made from the middle of the first proximal phalanx distally to the first cuneiform proximally halfway between the dorsal and plantar surfaces of the foot.

Deep Exposure of the First Metatarsal with Medial Eminence Removal and Bone Graft Preparation Capsule elevation of the first metatarsophalangeal joint allows medial eminence exposure, soft tissue removal, and then bone slices are harvested, staying 1 mm medial to the parasagittal groove, and preserving the bone graft in a receptacle. The first cuneiformmetatarsal joint is identified, and periosteal elevation is done of the future osteotomy site of the proximal one-quarter of the metatarsal shaft on its medial side, extending the elevation of the periosteum onto the superior and inferior surfaces.

IM Pinning

With the first metatarsal head held in the plantar flexed and supinated corrected position, a K wire is drilled in the coronal plane through the first metatarsal neck across the one-two interspace and through the second metatarsal neck. Further advancement of the K wire, holding the third metatarsal head depressed, allows the K wire to exit on the skin on dorsum of the foot. Using needle-nose pliers and a Frazier suction tip, the pin is bent, protecting the second metatarsal from fracture. The lateral end of the pin is bent dorsally, and the pin is then retracted medially until the bent end of the pin lodges on the fibular side of the second metatarsal neck.

The Chevron Cut

A horizontal proximal chevron osteotomy is made through the first metatarsal 1 cm distal to the first cuneiformmetatarsal joint, the point of the V being 1 cm distal to the joint. The osteotomy is done in the coronal plane, in the form of a V. Viewed from the medial side of the metatarsal, the point of the V is proximal. Each limb of the V extends forward, one forward and dorsally, and other forward and plantarly. The V goes all the way across the metatarsal.

First Metatarsal Displacement

Using the intermetatarsal pin as a guide rail and holding the osteotomy site so it can rotate into a valgus opening, the first metatarsal head is displaced laterally into the corrected position, opening the osteotomy V at its medial end. The correction will include valgus correction and pronation deformity correction, and it will avoid the pitfalls of excessive shortening of the first metatarsal and dorsal displacement of the first metatarsal at the osteotomy site.

X-ray

An x-ray is taken to verify appropriate correction.

Bone Graft

If the correction is adequate, bone graft slices are inserted in the upper and lower limbs of the chevron osteotomy at their medial sides which have widened out with the valgus correction. The osteotomy fragments are retracted medially at the first cuneiform-metatarsal joint at this time. Pin or screw fixation is now applied to the grafted osteotomy site if necessary. For example, a K wire may be drilled from the distal part of the osteotomy through the graft into the proximal part, or a screw may be inserted distally and slightly dorsally and extending proximally and plantarly into the proximal end of the first metatarsal. No proximal mechanical fixation is necessary if the assemblage appears to be rigid at the time of the operation.

Bolt and Lock Nut Fixation

The bolt and lock nut are inserted in one of three ways:

A. The pin is removed and the bolt is pushed through the pinholes from medial to lateral. The lock nut is attached, and fixation is completed by tightening down the locking screw.

B. The pin is used as guide pin for a cannulated system. The pin is overdrilled, and the cannulated bolt is inserted over the pin. The nut is attached. The guide wire is removed, and the lock nut is tightened.

C. The pin may be left in place while a new drill hole is made through the first and second metatarsal necks, allowing the bolt to be inserted, the nut to be attached, fixation to be completed, and the pin to be removed.

Capsule Repair and Closure

These are performed in the usual fashion and accompanied by casting if necessary.

Figure 2:
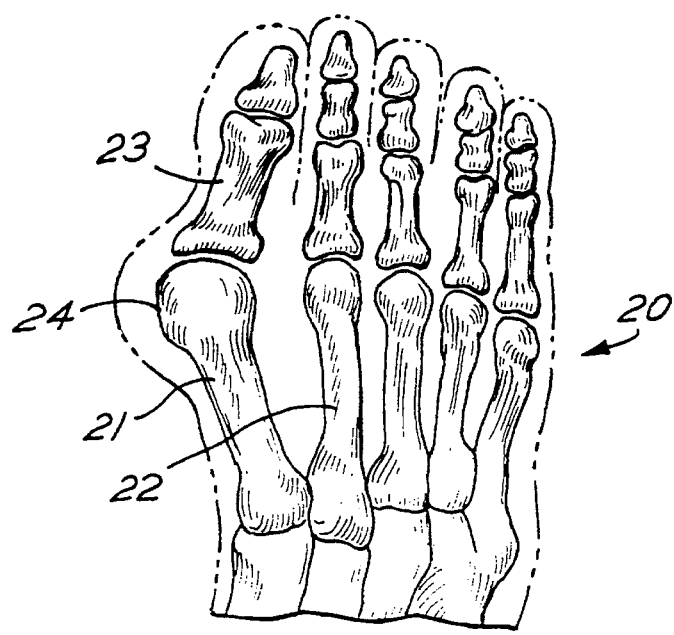
FIG. 2 is a dorsal view of the bones of a right forefoot afflicted with hallux valgus.

Referring now to the Figures, FIG. 1 illustrates, for comparative purposes, a dorsal view of the bones of a normal right forefoot 20 including the first metatarsal 21, second metatarsal 22 and first phalangeal bone 23. The intermetatarsal and hallux valgus angles are depicted in the figure. FIG. 2 demonstrates the type of change in forefoot bone orientation which is observed in patients with hallux valgus. In this forefoot 20, the medial eminence 24 of the first metatarsal 21 is particularly evident in its displaced position. The intermetatarsal and hallux valgus angles are clearly greater than those depicted in comparative FIG. 1.

Referring to FIG. 3, the medial eminence 24 is excised 26 in accordance with an aspect of the invention to leave to a newly cut bone surface 25 on the medial side of the distal end of the first metatarsal. FIG. 4 illustrates the insertion of the orthopedic drill bit 27 to drill a hole from the medial side of the first metatarsal 21 transversely through the bone approximately on the diameter of the cross section and out the lateral side, and similarly from the medial to the lateral side of second metatarsal 22 and out the lateral side.

FIG. 5 depicts the osteotomy cut 31 performed proximally on the first metatarsal to create proximal and distal first metatarsal segments 28 and 29 respectively. The invention also contemplates the intermetatarsal pinning during the osteotomy of the distal segment of the first metatarsal segment 29 to the second metatarsal 22 with stabilization device 30 which may or may not be the same as drill bit 27. FIG. 6 illustrates the osteotomy cut 31 and the stabilization device 30 from the medial view.

Shown in FIG. 7, the proximal segment of the first metatarsal 28 and the distal segment of the first metatarsal 29 are displaced relative to each other to compensate for the hallux valgus, creating a medial osteotomy gap 32. As illustrated in FIG. 8 pieces 26 of, the medial eminence which has been excised are next grafted into the gap.

Referring now to FIG. 9, the first metatarsal 21 is stabilized for healing by insertion of a fixation device 33 which splints the first metatarsal to the second metatarsal 22. The fixation device preferably includes a segment 34 which passes through the drill holes in the metatarsal bones. This segment of the fixation device should be relatively narrow in diameter as compared with the diameters of the first and second metatarsals, preferably on the order of ⅛ inch diameter. The fixation device should also be sized so as to span the distance from the medial side of the first metatarsal and out the lateral side of the second metatarsal when the bones have been reoriented in the correct fashion, preferably 1½ to 2 inches in length.

Referring to FIGS. 9, 10 and 11, the fixation device is in a preferred embodiment a bolt 33 having a head 35 located medially to the first metatarsal to retain its position. The bolt projects laterally beyond the second metatarsal neck and is fixed there with a locking means 39. Preferably, the bolt is coarsely threaded at its lateral end. The bolt may have a flattened longitudinal segment at its lateral end 40 and may be fitted when in position with a matching nut 39 which is cooperatively threaded to screw onto the lateral end of the bolt. The nut may be held in place by insertion of a set screw (not shown) through a radial hole in the nut to frictionally contact the flat surface 40 of the bolt, preventing casual loosening of the nut from the bolt.

Referring to FIGS. 12 and 13, the fixation device is illustrated in the embodiment of a bolt 33 with a head 35 which acts as the medial retainer member and a C-clamp 36 with tightening screw 37 which grips the lateral end of the bolt as a locking means.

With reference to FIGS. 14 and 15, the fixation device is illustrated in a preferred embodiment of an appropriately sized biocompatible bolt of the shoulder bolt style 41 with a head 42 which acts as a medial retainer member and a size-matched castle nut 43 which self locks on the lateral end of the bolt as a locking means.

After an appropriate healing period, the surgeon may remove some or all of the fixation device. Typically, the surgeon would make a small lateral incision to remove the locking nut and a small medial incision to extract the bolt.

The preferred embodiment of the present invention is now fully described. The above description, however, is only illustrative of the invention and is not intended to limit the invention in spirit or scope. Only the following claims and their equivalents limit the scope of the invention.

What is claimed is:

1. A surgical method for repair of hallux valgus comprising:
   (a) entering the tissues of the foot affected with hallux valgus using a medial incision at the first metatarsal;
   (b) excising the medial eminence of the first metatarsal head;
   (c) correcting the pronation deformity, maintaining the proper plantar displacement of the first metatarsal, and retaining these structures in position thereafter by mechanically linking the first and second metatarsal necks with a stabilization device and retaining said stabilization device in place during the remainder of the surgery;
   (d) thereafter performing a proximal chevron osteotomy on the first metatarsal shaft, forming two metatarsal segments;
   (e) reorienting the metatarsal segments relative to each other to compensate for the hallux valgus, thereby creating a medial dislocation gap at the terminus of the reoriented osteotomy surfaces;
   (f) grafting excised medial eminence tissue into the medial dislocation gap; and
   (g) stabilizing the reoriented first metatarsal during healing by replacing the stabilization device with a fixation device which splints the first metatarsal and links the first metatarsal to the second metatarsal and which is removable after healing, with limited trauma to surrounding tissues.

2. A method as in claim 1 further comprising making a dorsal incision on the foot performing a soft tissue release through the dorsal incision prior to performing said medial incision at the first metatarsal.

3. A method as in claim 1 wherein said step of retaining the first metatarsal in position by mechanically linking the first and second metatarsal necks comprises splinting the first metatarsal to the second metatarsal with a stabilization device before performing the proximal chevron osteotomy to retain the proper position and orientation of the first metatarsal during the remainder of the surgery.

4. A method as in claim 3 wherein the stabilization device is a biocompatible rigid pin.

5. A method as in claim 3 wherein the stabilization device is a K wire.

6. A method as in claim 1 further comprising removing the fixation device after healing.

7. A method as in claim 1 wherein the fixation device which splints the first metatarsal to the second metatarsal is a bolt with a C-clamp nut.

8. A method as in claim 1 wherein the fixation device which splints the first metatarsal to the second metatarsal is a bolt with a locking nut.

9. A method as in claim 1 wherein the fixation device which splints the first metatarsal to the second metatarsal is a shoulder bolt with a self-locking castle nut.

10. A surgical method for repair of hallux valgus comprising:
    (a) entering the tissues of the foot affected with hallux valgus using a medial incision at the first metatarsal;
    (b) excising the medial eminence of the first metatarsal head;
    (c) correcting the pronation deformity, maintaining the proper plantar displacement of the first metatarsal, and retaining these structures in position thereafter by mechanically linking the first and second metatarsal necks with a stabilization device and retaining said stabilization device in place during the remainder of the surgery;
    (d) thereafter performing a proximal chevron osteotomy on the first metatarsal shaft, forming two metatarsal segments;
    (e) reorienting the metatarsal segments relative to each other to compensate for the hallux valgus, thereby creating a medial dislocation gap at the terminus of the reoriented osteotomy surfaces;
    (f) grafting excised medial eminence tissue into the medial dislocation gap; and
    (g) stabilizing the reoriented first metatarsal during healing by retaining said stabilization device in a linked condition between said first and said second metatarsal necks, thereby stabilizing the reoriented first metatarsal during the post-operative healing period.

* * * * *